United States Patent [19]

Rohrbach

[11] Patent Number: 4,525,456

[45] Date of Patent: Jun. 25, 1985

[54] SUPPORT MATRIX AND IMMOBILIZED ENZYME SYSTEM

[75] Inventor: Ronald P. Rohrbach, Forest Lake, Ill.

[73] Assignee: UOP Inc., Des Plaines, Ill.

[21] Appl. No.: 439,958

[22] Filed: Nov. 8, 1982

[51] Int. Cl.[3] .................. C12N 11/14; C12N 11/02; C12N 11/08

[52] U.S. Cl. .................................. 435/176; 435/177; 435/180; 502/7

[58] Field of Search ............... 435/174, 176, 177, 180; 252/426, 428, 430; 502/7

[56] References Cited

U.S. PATENT DOCUMENTS

| | | | |
|---|---|---|---|
| 4,006,059 | 2/1977 | Butler | 435/176 |
| 4,141,857 | 2/1979 | Levy et al. | 252/430 |
| 4,235,973 | 11/1980 | Tschang et al. | 435/180 X |
| 4,434,228 | 2/1984 | Swann | 435/180 |

Primary Examiner—David M. Naff
Attorney, Agent, or Firm—James R. Hoatson, Jr.; Eugene I. Snyder; William H. Page, II

[57] ABSTRACT

A support matrix which immobilizes enzymes by ion exchange forces comprises a core support deposited on which is a functionalized polyethylenimine insoluble in water. Such support matrices may be prepared from a virtually limitless variety of core supports since the functionalized polyethylenimines of this invention show excellent adhesive properties even to smooth surfaces. Such support matrices are particularly useful where the enzyme to be immobilized has a rather limited inherent half-life. The functionalized polyethylenimine is a carboxylic acid amide of polyethylenimine, a sulfonic acid amide of polyethylenimine or polyalkylated polyethylenimine.

20 Claims, No Drawings

SUPPORT MATRIX AND IMMOBILIZED ENZYME SYSTEM

BACKGROUND OF THE INVENTION

In recent years the ability of enzymes to function as remarkably efficient chemical factories has been harnessed with considerable commercial success, in large part owing to increased technological competence in utilizing enzymes in immobilized enzyme systems. An immobilized enzyme system consists of a support matrix to which there is bound an enzyme. A support matrix is a structure characterized as having good physical integrity and favorable properties toward liquid flow under conditions experienced in fixed-bed reactors, and further characterized by having the ability to bind or immobilize enzymes with minimum perturbation of enzymatic action. By an immobilized enzyme system is meant the structure which results from immobilization of an enzyme on a support matrix.

An example of a support matrix and resulting immobilized enzyme system, and the one perhaps most closely related to the present invention, is that described in U.S. Pat. No. 4,141,857. The patentee's support matrix is a core support (porous inorganic oxide) impregnated with a polyamine subsequently cross-linked with an excess of a bifunctional reagent so as to provide excess pendant functional groups. One important characteristic of the prior art support matrix is that the polyamine is impregnated on porous material, with the polyamine in part deposited within the pores contributing to the surface of the support. Another important characteristic is that the polyamine is extensively cross-linked, including that part in the pores, thereby entrapping the material therein and firmly anchoring the resulting resin to the surface. The result is a resin, to which the enzyme is later bound, which is highly resistant to attrition, ablation, and other means of removal from the core support. It should be clear that there is a central role played by the pores of the support in giving rise to this latter property. Still another characteristic of this prior art is that the pendant functional groups become covalently bonded to enzymes, with the enzymes being firmly bound to the support matrix in the immobilized enzyme system. Such firm bonding is particularly useful when the inherent lifetime of the enzyme is long, that is, when physical removal would otherwise shorten the useful lifetime of the enzyme.

The advantages of the aforementioned prior art support matrix cannot be utilized in that class of enzymes whose inherent lifetime, as measured by its half-life under reaction conditions, is too short for such advantages to be experienced. Stated differently, a firm physical-chemical attachment of an enzyme and of the resin to a core support is irrelevant where the enzyme is deactivated faster than or competitively with the physical loss of enzyme and/or resin to which it is bound. The prior art support matrix advantages also cannot be fully utilized where its cost and the cost of immobilization is high relative to enzyme cost. That is, using a relatively inexpensive enzyme with a relatively expensive support matrix is not cost-effective. It is to these latter classes of enzymes that the present invention is particularly pertinent.

The invention here is a support matrix and immobilized enzyme system therefrom comprising a core support on the surface of which is deposited functionalized, water-insoluble polyethylenimine. In the support matrix of this invention the functionalized polyamine may be deposited on any surface; pores are unnecessary and superfluous not conferring any advantage. Another characteristic of this invention is that the functionalized polyamine is not cross-linked. Still another property is that the enzyme is bound by ion exchange forces, which are much weaker than the covalent bond of the prior discussed material. All these characteristics stand in bold contrast to the prior art.

The characteristics and differences alluded to in the preceding paragraph confer several distinct advantages to the support matrix of the present invention. One advantage is the simplicity of the composition and its preparation, both of which lead to substantial reduction in cost and time of preparation. Another advantage is that the support matrices are surface independent. That is, the support matrix and immobilized enzyme system may be prepared from a virtually unlimited number and nature of core supports in a variety of forms and shapes. Still another advantage is that the support matrix can be prepared with a uniform thickness of organic material serving as the enzyme binding material. Yet another important advantage of the materials of this invention is that after activity of the immobilized enzyme is reduced to the point of inutility the deactivated enzyme and the underlying binding material can be readily stripped or removed and the core support can be reused, thereby affording facile regeneration of the immobilized enzyme system. It is to be stressed that all these advantages confer maximum benefits when deactivation of the enzyme is at least competitive with physical loss of the enzyme from the immobilized enzyme system, or when the enzyme is relatively inexpensive, as elaborated upon above.

DESCRIPTION OF THE INVENTION

In one aspect the invention described herein is a support matrix comprising a core support on whose surface is deposited a water-insoluble functionalized derivative of polyethylenimine. In another aspect the invention is a method of preparing a support matrix comprising depositing a water-insoluble functionalized polyethylenimine selected from the group consisting of carboxylic and sulfonic acid amides and polyalkylated polyethylenimine on a core support, and recovering the resultant support matrix.

This invention is based on the observation that certain water-insoluble but organic solvent-soluble functionalized derivatives of polyethylenimine adhere readily to virtually any surface, thereby providing a thin film of uniform thickness of a functionalized polyethylenimine. The rationale behind this invention is to transform water-soluble polyethylenimine to a water-insoluble, organic solvent-soluble functionalized derivative of polyethylenimine. Stated differently, this invention is based in part upon functionalizing polyethylenimine to transform most of the amino centers to hydrophobic centers, leaving unchanged the tertiary amine sites which are responsible for ion exchange binding and which provide a hydrophilic environment for enzymes bound thereto.

Among the consequences of the invention described herein is that the materials may be deposited on any surface and may be almost literally painted on the surface. Consequently the support matrix is easy to prepare with a uniform film thickness. The materials described herein have good adhesive qualities; chemisorbtion is unnecessary for its binding. Another result is that spent or deactivated immobilized enzyme systems are readily stripped, as the functionalized polyethylenimines used in the practice of this invention are readily soluble in organic solvents. Consequently, a spent immobilized enzyme system can be contacted with a suitable organic solvent which will remove all organic material leaving the core support which may then be reused.

A core support is a physical structure with good mechanical integrity and which in a packed bed shows good flow properties toward aqueous systems. The core support must be chemically inert under conditions typical of enzyme conversion, but otherwise have no additional limitations in the practice of this invention. Among the core supports which may be used in the successful practice of this invention are inorganic oxides, glass, ceramics, metals, plastics, and membranes. It is to be emphasized that pores are unnecessary in the core support which may be used in this invention.

On the surface of the core support is deposited a functionalized polyethylenimine. Polyethylenimine is an article of commerce which is here defined as homopolymers of ethylenimine (aziridine) of molecular weight from about 1200 to about 100,000. Because of the cross-linking which accompanies homopolymerization a small fraction of the amino groups in polyethylenimine are tertiary, generally being no more than approximately 10% of the total.

The functionalized polyethylenimines used in this invention are polyalkylated polyethylenimines and the carboxylic and sulfonic acid amides of polyethylenimine. The nature and number of carboxyl or sulfonyl groups must be such as to render the resulting material hydrophobic and water-insoluble, but soluble in common organic solvents. Where the functionalized polyethylenimine is a carboxylic acid amide, the carboxylic acid function may be a saturated aliphatic carboxylic acid containing more than about four carbon atoms. Aromatic carboxylic acids also are satisfactory and are somewhat preferred. Examples of suitable carboxylic acids include pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, benzoic acid, naphthoic acid, phenylacetic acid, alkylated benzoic acids, halogenated benzoic acids, and so forth.

When the functionalized polyethylenimine is a sulfonic acid amide, the sulfonic acid is an aromatic sulfonic acid, including benzene and alkylbenzene sulfonic acids. Examples include benzene sulfonic acid, naphthalene sulfonic acid, toluene sulfonic acid, xylene sulfonic acid, ethylbenzene sulfonic acid, propylbenzene sulfonic acid, and so forth.

When a polyalkylated polyethylenimine is used, the alkyl group is a saturated aliphatic alkyl group containing at least eight carbon atoms. Examples of suitable alkyl groups include octyl, nonyl, decyl, undecyl, dodecyl, tridecyl, tetradecyl, pentadecyl, pentadecyl, hexadecyl, heptadecyl, octadecyl, nonadecyl, and eicosyl.

Whether the polyethylenimine is a polyamide or is polyalkylated, substantially all of the primary amino groups are substituted and more than about 50% of the secondary amino groups are substituted. This ensures suitable water-insolubility and hydrophobicity of the polyethylenimine, which are necessary attributes for the material to be successfully used in the practice of this invention.

The preparation of the functionalized polyethylenimines described above is well-known in the art. In all cases they are prepared by reacting slightly more than one molar proportion of the acylating, sulfonating, or alkylating agent per mole of primary plus secondary amino groups. Examples of acylating and sulfonating agents include their anhydrides and acid and sulfonic acid halides. Examples of alkylating agents include alkyl halides, sulfates and sulfonates, and so forth.

As an example, carboxylic acid amides may be prepared by reacting somewhat more than one mole of a suitable acid halide, such as benzoyl halide, with an amount of polyethylenimine furnishing one mole proportion of primary and secondary amine groups. This may be performed in aqueous solution using an aqueous base, typical of the Schotten-Baumann reaction conditions. The reaction also can be conducted in a nonaqueous solvent using a tertiary amine as the base.

The support matrix may be prepared by contacting the core support with a solution of the functionalized polyethylenimine in a common organic solvent. The choice of solvent is in no way critical to the success of this invention subject to the requirement that it be inert. It is advantageous that the solvent have a relativey low boiling point, under about 120° C. Among solvents which may be used are alcohols such as ethyl, propyl, and butyl alcohols, ketones such as acetone, methyl ethyl ketone, diethyl ketone, and so forth, ethers such as diethyl ether, dipropyl ether, tetrahydrofuran, and tetrahydropyran, esters such as methyl acetate, methyl propionate, ethyl acetate, and so forth, hydrocarbons such as benzene and toluene, and so forth. It is to be understood that the above solvents are merely illustrative and are not comprehensive.

The concentration of amine in the organic solvent is less than about 5%, and preferably from about 0.3 to about 2 percent by weight. The contact time of the core support with the organic solution of the functionalized polyethylenimine depends upon the nature of the support. In those cases where the support is nonporous it is sufficient to merely dip-drain the core support in the solution of the polyethylenimine and subsequently evaporate the organic solvent. Where the core support is somewhat porous it is advantageous to contact the support with the solution of functionalized polyethylenimine for a time up to about 1 hour. Solvent then needs to be removed by evaporation, such as by heating or by evaporation under reduced pressure.

Illustrative of the enzymes which may be used in the practice of this invention are glucoamylase, alpha-amylase, beta-amylase, pullulanase, lactase, rennin, glucose oxidase, protease, lipase, urease, arginase, asparaginase, catalase, chymotrypsin, cellulase, peroxidase, lysozyme, and papain.

Enzyme immobilization is performed by contacting the support matrix with an aqueous solution of the enzyme for a time and at a temperature at which enzyme deactivation is minimized. Generally, the support matrix and a dilute (1–10%) solution of the enzyme are contacted at a temperature at or below ambient for a time from about 4–16 hours. Excess solution is removed, as by decantation, and the resulting material is washed with water to remove adhering but unbound enzyme.

The following example is merely illustrative of this invention and should not be construed to limit it in any way.

EXAMPLE

To a solution of 10 g polyethylenimine (molecular weight ca. 70,000) in 130 ml water containing 5 ml of 50% sodium hydroxide was slowly added 10 ml of benzoyl chloride. The reaction was permitted to continue for about one hour after the initial appearance of solid, at which time solid was collected by filtration. The solid was washed well with water, air dried, and dissolved in chloroform to which was added anhydrous magnesium sulfate to remove any remaining water. The chloroform mixture was filtered and hexane was added to the filtrate to precipitate benzoylated polyethylenimine.

Alumina (1 g, 60/80 mesh) was added to 10 ml of a 1% solution of benzoylated polyethylenimine in ethanol. After one hour solid is removed by filtration and air dried to afford the support matrix.

The aforedescribed support matrix is contacted, with occasional mixing, with an aqueous solution of glucoamylase at 14 units per ml. After 16 hours at 4° C. solid is collected by filtration and washed well with water to remove loosely adhering enzyme. The immobilized glucoamylase thus prepared had an activity of 38 units per g at 60° C.

What is claimed is:

1. A method of preparing a support matrix comprising depositing a water-insoluble functionalized polyethylenimine, where the polyethylenimine has a molecular weight from about 1200 to about 100,000, selected from the group consisting of carboxylic acid amides of polyethylenimine, sulfonic acid amides of polyethylenimine, and polyalkylated polyethylenimine on a core support, and recovering the resulting support matrix.

2. The method of claim 1 where the functionalized polyethylenimine is a carboxylic or sulfonic acid amide of polyethylenimine wherein substantially all primary amino groups and a major proportion of the secondary amino groups have been converted to amides.

3. The method of claim 2 where the carboxylic acid is a saturated aliphatic carboxylic acid containing more than about 4 carbon atoms.

4. The method of claim 2 where the carboxylic acid is an aromatic carboxylic acid.

5. The method of claim 4 where the acid is benzoic acid.

6. The method of claim 2 where the sulfonic acid is an aromatic sulfonic acid.

7. The method of claim 6 where the acid is benzene sulfonic acid.

8. The method of claim 6 where the acid is toluene sulfonic acid.

9. The method of claim 1 where the core support is selected from the group consisting of inorganic oxides, glass, ceramics, metals, plastics and membranes.

10. A support matrix comprising a core support on whose surface is deposited a water-insoluble functionalized derivative of polyethylenimine, where the polyethylenimine has a molecular weight from about 1200 to about 100,000, selected from the group consisting of carboxylic acid amides of polyethylenimine, sulfonic acid amides of polyethylenimine, and polyalkylated polyethylenimne.

11. The support matrix of claim 10 where the functionalized polyethylenimine is a carboxylic or sulfonic acid amide of polyethylenimine wherein substantially all the primary amino groups and a major proportion of the secondary amino groups have been converted to amides.

12. The support matrix of claim 11 where the carboxylic acid is a saturated aliphatic carboxylic acid containing more than about 4 carbon atoms.

13. The support matrix of claim 11 where the carboxylic acid is an aromatic carboxylic acid.

14. The support matrix of claim 13 where the acid is benzoic acid.

15. The support matrix of claim 11 where the sulfonic acid is an aromatic sulfonic acid.

16. The support matrix of claim 15 where the acid is benzene sulfonic acid.

17. The support matrix of claim 15 where the acid is toluene sulfonic acid.

18. The support matrix of claim 10 where the core support is selected from the group consisting of inorganic oxides, glass, ceramics, metals, plastics and membranes.

19. An immobilized enzyme system comprising the support matrix of claim 10 to which there is bound an enzyme.

20. The immobilized enzyme system of claim 19 where the enzyme is selected from the group consisting of glucoamylase, alphaamylase, beta-amylase, pullulanase, lactase, rennin, glucose oxidase, protease, lipase, urease, arginase, asparaginase, catalase, chymotrypsin, cellulase, peroxidase, lysozyme, and papain.

* * * * *